(12) United States Patent
Scheller et al.

(10) Patent No.: US 6,966,921 B2
(45) Date of Patent: Nov. 22, 2005

(54) DEVICE FOR RADIAL OPTIC NEUROTOMY

(75) Inventors: Gregg Scheller, Wildwood, MO (US); E. Mitchel Opremcak, Columbus, OH (US)

(73) Assignee: Synergetics, Inc., St. Charles, MO (US)

( * ) Notice: Subject to any disclaimer, the term of this patent is extended or adjusted under 35 U.S.C. 154(b) by 77 days.

(21) Appl. No.: 10/625,434

(22) Filed: Jul. 23, 2003

(65) Prior Publication Data

US 2004/0133224 A1   Jul. 8, 2004

Related U.S. Application Data

(60) Provisional application No. 60/397,793, filed on Jul. 24, 2002.

(51) Int. Cl.[7] ............................................. A61B 17/32
(52) U.S. Cl. ..................................................... 606/166
(58) Field of Search ............................... 606/166, 107, 606/184, 167, 185, 170, 172, 174

(56) References Cited

U.S. PATENT DOCUMENTS

5,203,865 A  *  4/1993  Siepser ........................ 606/166
6,663,644 B1 * 12/2003  Ross et al. .................. 606/166

OTHER PUBLICATIONS

Opremcak, et al., Radial Optic Neurotomy for Central Retinal Vein Occlusion, Journal of Retinal and Vitreous Diseases, 2001, vol.21, No. 5, Figs. 1 & 2, Showing a conventional Microvitreoretinal Blade (MVR blade).

* cited by examiner

Primary Examiner—Kevin T. Truong
(74) Attorney, Agent, or Firm—Kevin L. Klug

(57) ABSTRACT

A device for radial optic neurotomy comprising a radial optic neurotomy knife and its method of use. Comprising in a preferred embodiment, a uniquely formed asymmetrical "V" shaped tip having a first sharpened leg and a second dulled leg and a depth gauge. In a preferred embodiment said depth gauge comprises a laser mark which is substantially perpendicular with a central axis of a tip holding shaft. The device is specially designed for performing the radial optic neurotomy (RON) surgical procedure and thereby promoting relaxation of the scleral outlet.

20 Claims, 5 Drawing Sheets

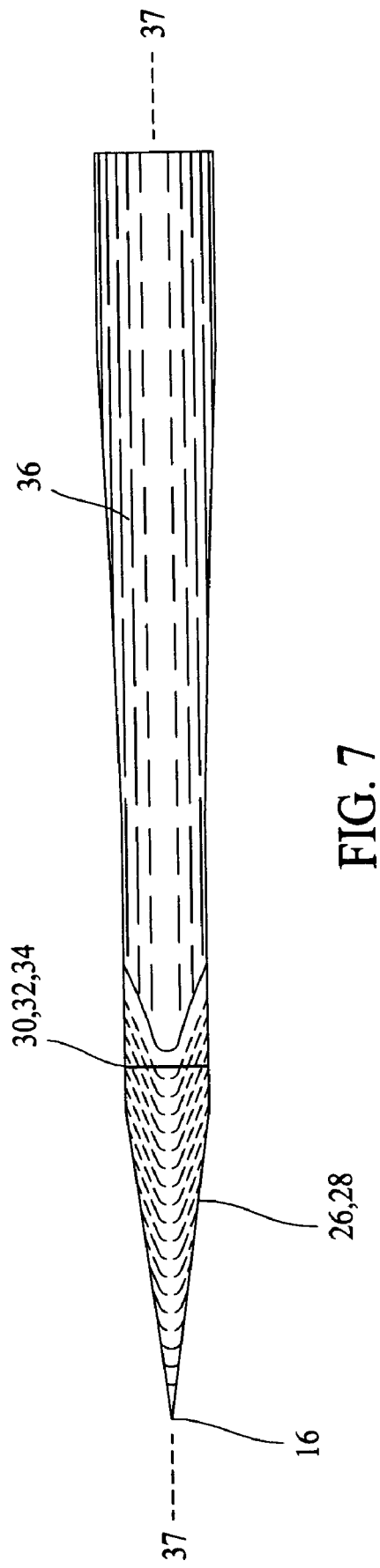
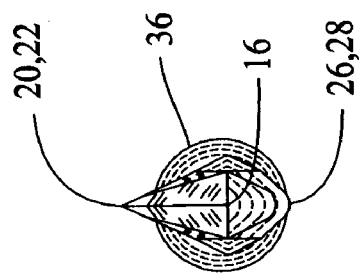
FIG. 7
FIG. 6

DEVICE FOR RADIAL OPTIC NEUROTOMY

This application claims priority of Provisional Patent Application No. 60/397,793, filed Jul. 24, 2002.

BACKGROUND OF THE INVENTION

The art of the present invention relates to eye surgical devices in general and more particularly to an improved and modified form of a microvitreoretinal (MVR) blade having elements and features especially suited for radial optic neurotomy (RON) as a treatment for central retinal vein occlusion (CRVO).

Central retinal vein occlusion (CRVO) is a relatively common condition, reported to occur in approximately 60,000 new patients each year within the United States. Its etiology is poorly understood, with a wide array of medical and systemic disorders debated as to their potential causative effect. CRVO is most commonly reported in patients aged 50 to 80 years, with a statistical tendency towards those patients suffering from hypertension and/or glaucoma. The natural history of this condition can result in loss of vision due to extensive intraretinal hemorrhage, macular edema, iris neovascularization, neovascular glaucoma, and ischemic retinal infarct. Spontaneous resolution is uncommon; rather, it is most widely reported to have catastrophic consequences to affected patients.

There is no effective curative therapy for CRVO. Panretinal photocoagulation can be effective in controlling neovascularization, while grid photocoagulation has been reported to be successful in resolving edema. However, neither therapy restores vision nor reverses the basic occlusive condition. Attempts to create a physiological shunt by way of a of high powered photocoagulating chorioretinal anastomosis has reported some success, but is similarly associated with a high rate of complications. Many theorize that the CRVO is associated with thrombus within the central retinal vein. As such, many developing therapies have concentrated on resolving the thrombus by means of cannulation of the central retinal vein and administration of "clot busting" agents (t-PA). While technically feasible, the clinical results and reproducibility of this procedure remain non-validated.

An emerging hypothesis suggests that CRVO is a vascular complication secondary to a compartment syndrome. This condition is created as the optic nerve enters the eye, experiencing a reduction in outer diameter from 3.0 mm to 1.5 mm at the optic nerve head. It is theorized that congenital anatomical variances, connective tissue, persistent myelin sheaths, ocular motion, and other factors may increase pressure within the scleral outlet-compartment, thereby resulting in CRVO.

A new surgical procedure, radial optic neurotomy, (RON) addresses this causative factor and, in so doing, potentially provides a curative effect. By inserting a knife radial to the optic nerve head and advancing a specified distance, the compartment syndrome may be relieved by relaxing the cribiform plate, scleral ring, and adjacent sclera. Unfortunately, the greatest potential complication of such a maneuver is hemorrhage. To address this complication, the present art device incorporates design elements and features which minimize this threat.

The present art device is best described as a radial optic neurotomy (RON) knife. The device comprises in its most basic form, a modified conventional microvitreoretinal (MVR) blade with a single sharp nasal portion edge rather than the two opposing sharp edges, both nasally and medially as found in conventional MVR blades. Prior art conventional microvitreoretinal (MVR) knives or blades introduce a significant risk during the RON procedure as the sharp nasal and medial edges may cause an inadvertent disruption or cutting of the central retinal vessels. The single sharp edge of the present art device allows for a radial incision of the optic nerve head, with the incision proceeding nasally. In the present art device, the medial edge, i.e. the edge opposite the single sharp edge, of the blade is specially dulled, thereby allowing atraumatic passage of the knife alongside the central retinal artery and central retinal vein. The present art device further provides a depth gauge or measuring technique via the inclusion of a mark at a desired penetration depth distance from the device tip. Prior art conventional microvitreoretinal (MVR) knives or blades are unmarked, thereby leaving the surgeon without indication as to the actual depth of penetration. This mark provides the surgeon with a specific reference as to the depth of the radial incision, thereby minimizing the potential for globe perforation.

Accordingly, it is an object of the present invention to provide a device for radial optic neurotomy having a sharp edge and a medial dulled edge which is capable of atraumatic passage alongside the central retinal artery and central retinal vein.

Another object of the present invention is to provide a device for radial optic neurotomy having a depth gauge or measuring technique to optimize a desired penetration depth.

SUMMARY OF THE INVENTION

To accomplish the foregoing and other objects of this invention there is provided a device for radial optic neurotomy. The apparatus is especially suited for use with and during the radial optic neurotomy procedure.

The present art device or RON blade first comprises a substantially asymmetrical "V" shaped tip having a distal point, the base or point of said "V" substantially representing the distal end of the present device. In the preferred embodiment, the top or broad portion of said "V" shaped tip is attached with a tip holding shaft having a proximally attached handle. Said asymmetrical "V" shaped tip comprises a first leg of said "V" having the single sharp edge and a second leg of said "V" opposite said first leg comprising a burnished, dulled, or rounded edge.

The preferred embodiment further places a laser mark onto both broad sides of said "V" shaped tip transitional taper area to function as a depth gauge. Again in the preferred embodiment, said laser mark is in the form of a line which is substantially perpendicular with the central shaft axis. Alternative embodiments may place one or more of said marks at any location which would indicate the proper depth of penetration during surgical use or place multiple marks to accommodate varying pathology and/or surgical nuances. Alternative embodiments may further utilize said mark as a partial line or other mark form which is scribed or marked in a fashion other than laser marking or which is positioned in a fashion which is not perpendicular with the central shaft axis or which is located onto only one side.

As aforesaid, a handle or grip attaches with said central shaft opposite said "V" shaped tip and proximal to the user. Preferably said handle or grip is cylindrical in form, but may take many forms or shapes which allow a surgeon to easily utilize the device. The present art device is claimed as the tip in conjunction with the attached shaft and as a further embodiment, the tip with attached shaft and handle or grip.

The "V" shaped tip of the present device may be manufactured from a plurality of materials, these include but are not limited to stainless steel, diamond, both natural and/or synthetic, ruby, obsidian, ceramic, or nickel-titanium alloys. In the preferred embodiment, the shaft is manufactured from stainless steel and the handle or grip is manufactured from a durable high temperature polymer capable of withstanding autoclave temperatures. The shaft and handle may further be manufactured from any material which is biologically safe for surgical use and further provides the lateral and torsional strength required for surgical use. Further embodiments may also utilize an anti-reflective surface treatment, coating, or process on the tip or shaft.

BRIEF DESCRIPTION OF THE DRAWINGS

Numerous other objects, features and advantages of the invention should now become apparent upon a reading of the following detailed description taken in conjunction with the accompanying drawings, in which:

FIG. 6 front side plan view thereof of a preferred embodiment showing the "V" shaped tip and tip holding shaft.

FIG. 7 is a bottom side plan view thereof of a preferred embodiment showing the rounded edge of the "V" shaped tip and tip holding shaft.

DETAILED DESCRIPTION

Figure 1:
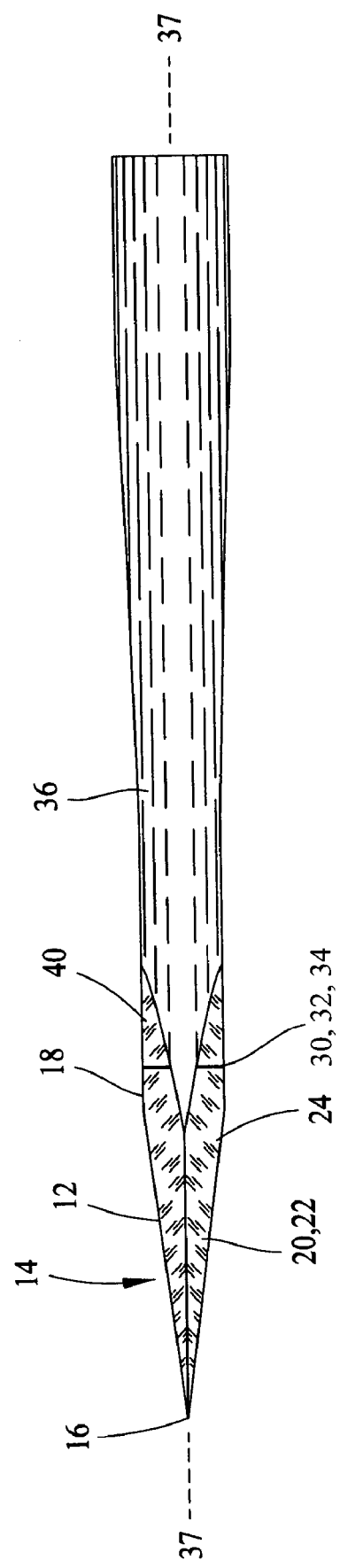
FIG. 1 is a top plan view of a preferred embodiment of the device for radial optic neurotomy showing the substantially "V" shaped tip with laser mark and tip holding shaft.
Figure 2:
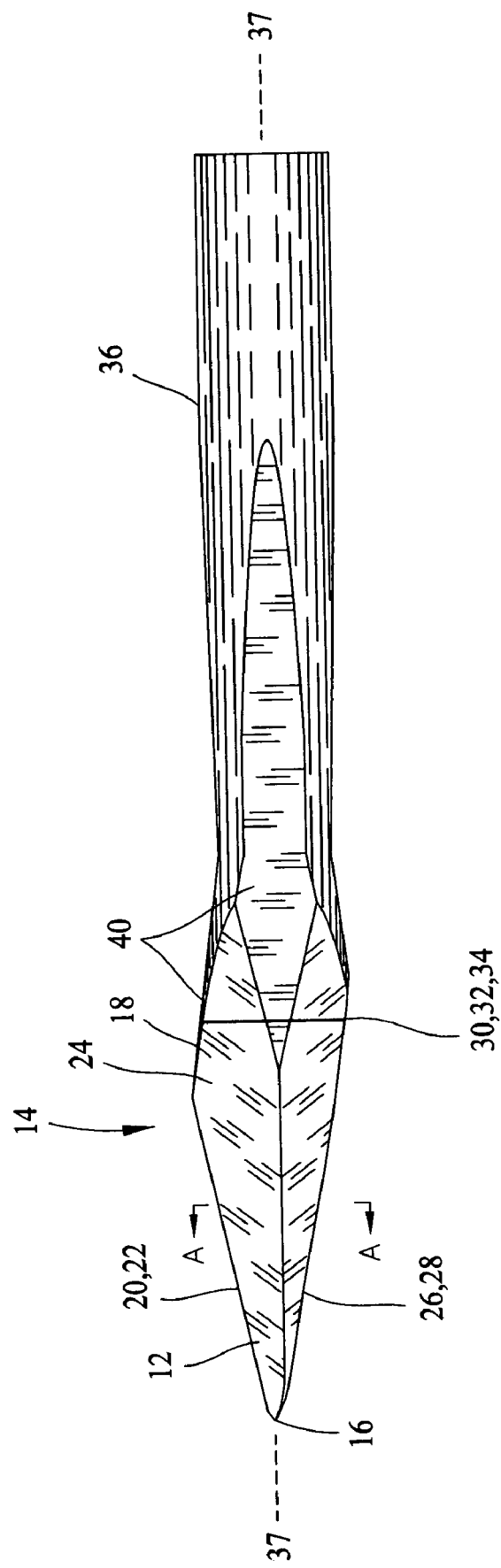
FIG. 2 is a left side plan view thereof, which is symmetrical with a right side plan view, of the device for radial optic neurotomy showing the substantially "V" shaped tip with laser mark and tip holding shaft.
Figure 4:
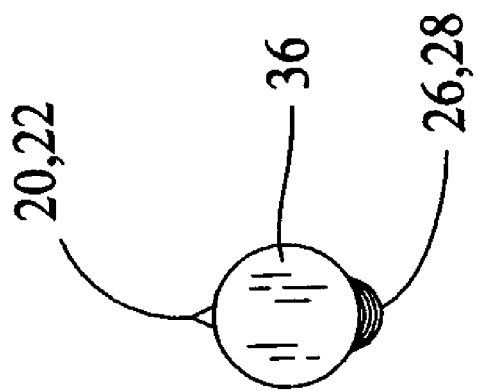
FIG. 4 is a rear side plan view thereof without attached handle or grip.
Figure 3:
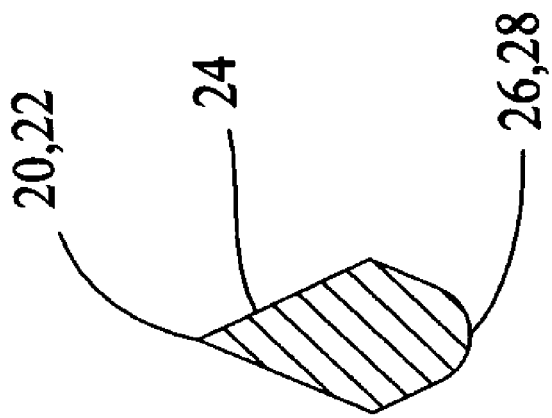
FIG. 3 is a cross sectional view thereof taken along line 3—3 in FIG. 2.
Figure 5:
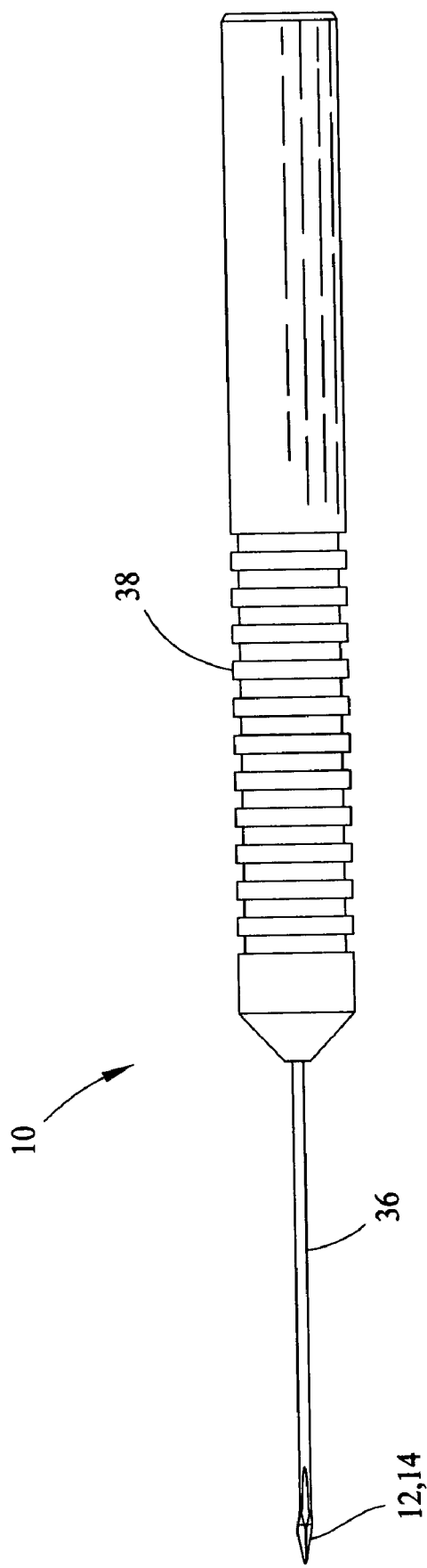
FIG. 5 is a left side perspective view thereof of a preferred embodiment fully showing the substantially "V" shaped tip with laser mark, tip holding shaft, and handle or grip, all of which is substantially symmetric with a right side perspective view.

Referring now to the drawings, there is shown in FIGS. 1–7 a preferred embodiment of a device for radial optic neurotomy 10 having a blade 12 with a sharp edge 22 on a first leg 20 and a dulled edge 28 on a second leg 26 and a depth gauge 30 placed distally from a point 16 of said blade 12. The device for radial optic neurotomy 10 is particularly adapted to relieve the aforesaid compartment syndrome during the radial optic neurotomy, (RON) procedure with a minimal risk of hemorrhage.

The present art device for radial optic neurotomy 10 first comprises a substantially a symmetrical "V" shaped tip 14 having a distal point 16, the base or point 16 of said "V" substantially representing the distal end of the present device. In the preferred embodiment, the top or broad portion 18 of said "V" shaped tip is attached with a tip holding shaft 36 having a proximally attached handle 38. Said asymmetrical "V" shaped tip comprises a first leg 20 of said "V" having the single sharp edge 22 and a second leg 26 of said "V" opposite said first leg 20 comprising a burnished, dulled, or rounded edge 28. In a preferred embodiment, said first leg represented by said first single sharp edge 22 is angled approximately 12 degrees from the central axis 37 of said tip holding shaft 36. Also in a preferred embodiment, said second leg 26 represented by said dulled or rounded edge 28 is angled approximately 10 degrees from the central axis 37 of said tip holding shaft 36, said angle rotationally opposite said first leg 20. Alternative embodiments may vary the aforementioned angles considerably without departing from the scope and spirit of the present invention. In the preferred embodiment, the second leg 26 deviates from said 10 degrees as it approaches the base or point 16 of said "V" (i.e. distal end), thereby forming an angle of approximately 30 degrees relative to the central shaft axis 37. This deviation further places said second leg 26 or dulled edge 28 slightly across the central shaft axis 37 and toward the first leg 20 or sharpened edge 22, thereby shifting the distal point 16 across the central shaft axis 37 toward said first leg 20 or sharp edge 22. The aforementioned deviation further ensures that the device 10 and the distal point 16 shall only cut on one side, i.e. the first leg 20 or sharp edge 22, when inserted near said optic nerve head. The aforesaid 30 degree deviation may be varied considerably without departing from the scope of the present invention provided that the aforementioned benefits are maintained. Alternative embodiments may provide said dulled second leg edge 28 without shifting said second leg 26 across the central shaft axis 37.

In the preferred embodiment, the sharpened edge 22 is formed from a substantially linear taper plane 24 positioned from a line substantially parallel with said central axis 37 toward the first leg 20 of said "V" 14. Alternative embodiments may provide said first leg 20 sharpened edge 22 without the aforesaid taper 24, provided said first leg 20 sharpened edge maintains the aforesaid cutting characteristics.

In the preferred embodiment, the tip holding shaft 36 is slightly smaller in diameter or width than the top or broad portion of said "V" shaped tip 14. This configuration requires that the tip attachment with said tip holding shaft 36 transitionally taper 40 to the shaft 36 dimensions. In the preferred embodiment, this transitional taper 40 does not contain a sharpened edge. Alternative embodiments may eliminate said transitional taper 40 or place a sharpened edge on the first leg 20 side of said transitional taper 40. The second leg 26 side of said transitional taper 40 further maintains the dulled or rounded edge 28 to avoid cutting action on the second leg 26 side.

The preferred embodiment further places a laser mark 34 onto both broad 18 sides of said "V" shaped tip 14 transitional taper 40 area to function as a depth gauge 30. Again in the preferred embodiment, said laser mark 34 is in the form of a line 32 which is substantially perpendicular with the central shaft axis 37. Alternative embodiments may place on or more of said marks 34 at any location which would indicate the proper depth of penetration during surgical use or place multiple marks to accommodate varying pathology and/or surgical nuances. Alternative embodiments may further utilize said mark 34 as a partial line or other mark form which is scribed or marked in a fashion other than laser marking or which is positioned in a fashion which is not perpendicular with the central shaft axis or which is located onto only one side.

In one form of the preferred embodiment, the first leg 20 or sharpened edge 22 is approximately 0.090 inches, the laser mark 34 is positioned proximally from the distal point approximately 0.108 inches or 2.7 millimeters, the broad portion 18 of said "V" shaped tip 14 is approximately 0.0465 inches wide at its widest portion, the tip holding shaft 36 is approximately 0.033 inches in diameter, and the distal point 16 is shifted across the central shaft axis 37 toward said first leg 20 or sharp edge 22 by 0.003 inches. The aforesaid dimensions are given for enablement purposes only and do not singularly represent the preferred embodiment. Alternative embodiments may vary the aforesaid dimensions considerably provided the first leg 20 sharpened edge 22 and second leg 26 dulled edge 28 characteristics are maintained.

As aforesaid, a handle or grip 38 attaches with said central shaft 36 opposite said "V" shaped tip 14 and proximal to the user. Preferably said handle or grip 38 is cylindrical in form, but may take many forms or shapes which allow a surgeon to easily utilize the device. The present art device is claimed as the tip 14 in conjunction with the attached shaft 36 and as a further embodiment, the tip 14 with attached shaft 36 and handle or grip 38.

During utilization of the radial optic neurotomy device 10, the surgeon inserts the asymmetrical "V" shaped tip 14 radial to the optic nerve head and advances said tip 14 a specified distance thereby relieving the compartment syndrome and relaxing the cribiform plate, scleral ring, and adjacent sclera. In order to minimize hemorrhage and other complications, the first leg 20 sharp edge 22 is positioned whereby a radial incision proceeds nasally to or away from the optic nerve head and the second leg 26 dulled edge 28 proceeds alongside or near the optic nerve head, central retinal artery, or central retinal vein without incision promotion, thereby allowing atraumatic passage of the device 10.

Those skilled in the art will appreciate that a radial optic neurotomy (RON) knife utilized for surgical decompression of central retinal vein occlusion (CRVO) has been shown and described. That said present art is capable of providing a radial incision on the nasal aspect of the optic nerve head, a relaxing incision to the scleral ring and cribiform plate by means of an extremely sharp edge on the nasal portion of the device. The device further provides an atraumatic passage of the knife past the central retinal vessels due to a burnished and dulled or rounded medial edge. The present art may further be utilized in general retinovascular ophthalmic surgery.

Having described the invention in detail, those skilled in the art will appreciate that modifications may be made of the invention without departing from its spirit. Therefore, it is not intended that the scope of the invention be limited to the specific embodiments illustrated and described. Rather it is intended that the scope of this invention be determined by the appended claims and their equivalents.

What is claimed is:

1. A radial optic neurotomy knife comprising:
   a blade having an asymmetrical "V" shaped tip having a distal point at a distal end of said blade; and
   an outermost first leg of said "V" having a first angle relative to a central axis of a tip holding shaft; and
   an outermost second leg of said "V" having a second angle relative to said central axis rotationally opposite said first leg angle; and
   said distal point substantially near said central axis; and
   said "V" shaped tip having said distal point opposite a broad portion, said first leg of said "V" shape having a sharpened edge, and said second leg of said "V" shape having a dulled edge; and
   said tip holding shaft having said central axis, a first end, and a second end attached with said broad portion of said "V" shaped tip via a transitional taper, said transitional taper distinct from said asymmetrical "V" shaped tip.

2. The radial optic neurotomy knife as set forth in claim 1 further comprising:
   a depth gauge positioned substantially with said blade whereby depth of penetration of said blade is monitored.

3. The radial optic neurotomy knife as set forth in claim 2 said depth gauge further comprising:
   one or more lines placed onto said blade at a user desirable distance from said point.

4. The radial optic neurotomy knife as set forth in claim 3 whereby:
   one or more of said lines of said depth gauge are formed by laser marking.

5. The radial optic neurotomy knife as set forth in claim 2 said depth gauge further comprising:
   one or more lines placed substantially perpendicular to said central axis of said tip holding shaft and between said point and said tip holding shaft.

6. The radial optic neurotomy knife as set forth in claim 1 further comprising:
   a handle of substantially cylindrical form connected near said first end of said tip holding shaft.

7. The radial optic neurotomy knife as set forth in claim 1 whereby:
   said sharpened edge of said first leg of said "V" shape is substantially formed from one or more linear tapers extending from substantially near said central axis of said tip holding shaft toward said first leg.

8. The radial optic neurotomy knife as set forth in claim 1 whereby:
   said first leg is angled approximately 12 degrees from the central axis of said tip holding shaft.

9. The radial optic neurotomy knife as set forth in claim 8 whereby:
   said second leg is angled approximately 10 degrees from the central axis of said tip holding shaft.

10. The radial optic neurotomy knife as set forth in claim 9 whereby:
    said second leg deviates from said 10 degrees as it approaches said point of said "V" shape to an angle of approximately 30 degrees relative to said central shaft axis.

11. The radial optic neurotomy knife as set forth in claim 10 whereby:
    said second leg deviation is further placed slightly across said central shaft axis toward said first leg and said point is located across said central shaft axis toward said first leg.

12. The radial optic neurotomy knife as set forth in claim 9 whereby:
    said second leg deviates slightly across said central shaft axis toward said first leg and said point is placed across said central shaft axis toward said first leg.

13. The radial optic neurotomy knife as set forth in claim 1 whereby:
    said tip holding shaft is slightly smaller in a diameter or a width than said broad portion of said "V" shape and said transitional taper is placed between said "V" shape and said tip holding shaft.

14. The radial optic neurotomy knife as set forth in claim 3 whereby:
    said first leg is approximately 0.090 inches in length and one or more of said lines are positioned proximally from said point approximately 0.108 inches, and said point is positioned across said central shaft axis toward said first leg approximately 0.003 inches.

15. A radial optic neurotomy knife for performing a radial optic neurotomy procedure comprising:

an asymmetrical "V" shaped tip having a distal point and a broad portion substantially opposite said point, a first leg of said "V" shape having a sharpened edge, and a second leg of said "V" shape having a dulled edge rotationally opposite said first leg; and a tip holding shaft having a central axis, a width less than said broad portion of said "V" shaped tip, a first end having an attached handle, and a second end attached with a transitional taper substantially near said broad portion of said "V" shaped tip; and a depth gauge in the form of one or more lines placed onto said asymmetrical "V" shaped tip or said transitional taper, whereby depth of penetration of said blade is monitored.

16. The radial optic neurotomy knife for performing a radial optic neurotomy procedure as set forth in claim 15 whereby:

one or more of said lines forming said depth gauge comprise laser marks.

17. The radial optic neurotomy knife for performing a radial optic neurotomy procedure as set forth in claim 15 whereby:

said point of said asymmetrical "V" shaped tip is located slightly across said central shaft axis toward said first leg and said second leg extends slightly across said central shaft axis toward said first leg.

18. A method of performing a radial optic neurotomy surgical procedure as a treatment for central retinal vein occlusion, the steps comprising:

forming an asymmetrical "V" shaped tip having a point and a broad portion and a first leg having a sharpened edge and a second leg having a dulled edge; and forming a transitional taper near said broad portion extending away from said point; and connecting said transitional taper opposite said broad portion with a tip holding shaft having a central axis and an attached handle; and placing said point substantially near said central axis; and inserting said "V" shaped tip point radial to an optic nerve head whereby said dulled edge is nearest said optic nerve head; and advancing said "V" shaped tip a specified distance; and atraumatically passing said dulled edge of said "V" shaped tin alongside a central retinal artery and a central retinal vein whereby a compartment syndrome may be relieved by relaxing a cribiform plate, a scleral ring, or an adjacent sclera thereby reducing the possibility of hemorrhage.

19. The method of performing a radial optic neurotomy surgical procedure as a treatment for central retinal vein occlusion as set forth in claim 18 further comprising:

forming a depth gauge with said "V" shaped tip or said transitional taper; and reading said depth gauge as said "V" shaped tip is inserted; and limiting said inserting of said "V" shaped tip pursuant to said reading of said depth gauge whereby said specified distance of said "V" shaped tip advancing is achieved.

20. The method of performing a radial optic neurotomy surgical procedure as a treatment for central retinal vein occlusion as set forth in claim 19 said forming of said depth gauge further comprising:

forming one or more lines on said "V" shaped tip or said transitional taper substantially perpendicular with said central axis of said tip holding shaft.

* * * * *